United States Patent [19]

Ferguson et al.

[11] Patent Number: 4,935,542
[45] Date of Patent: * Jun. 19, 1990

[54] NAPHTHENIC ACID AMIDES

[75] Inventors: Sam Ferguson, Sugar Land; Darrell D. Reese, Richmond, both of Tex.

[73] Assignee: Nalco Chemical Company, Naperville, Ill.

[*] Notice: The portion of the term of this patent subsequent to May 20, 2003 has been disclaimed.

[21] Appl. No.: 274,565

[22] Filed: Nov. 22, 1988

Related U.S. Application Data

[63] Continuation-in-part of Ser. No. 51,558, May 18, 1987, Pat. No. 4,827,033.

[51] Int. Cl.$^5$ ............................................. C07C 233/18
[52] U.S. Cl. ..................................... 564/123; 564/188
[58] Field of Search ................................. 564/188, 123

[56] References Cited

U.S. PATENT DOCUMENTS 4,589,979  5/1986  Ferguson et al. ................... 208/263

Primary Examiner—Glennon H. Hollrah
Assistant Examiner—Amelia A. Owens
Attorney, Agent, or Firm—John G. Premo; Donald G. Epple; Anthony L. Cupoli

[57] ABSTRACT

A method of producing naphthenic acid having the formula

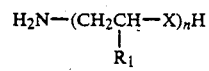

where
$R_1$ is H or Me,
X is chosen, at each occurrence, from O or NH, and
n is a small whole number of from 1–10, which comprises reacting an amine of the formula

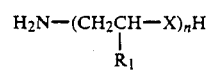

where
$R_1$ is H or Me,
X is chosen, at each occurrence, from O or NH, and
n is a small whole number of from 1–10, with a petroleum fraction containing naphthenic acids to form a salt and then heating the petroleum fraction containing the naphthenic acid-amine salt to a temperature of at least 25° F. greater than the boiling point of water for a time sufficient to convert the amine salts to the amides and then recovering the thus produced amides.

1 Claim, No Drawings

NAPHTHENIC ACID AMIDES

This is a continuation-in-part of our application Ser. No. 051,558, filed May. 18, 1987 now U.S. Pat. No. 4,827,033.

INTRODUCTION

U.S. Pat. No. 4,589,979, which is incorporated herein by reference, discloses a method for neutralizing the organic acidity in heavy gas oils. The invention is described in this patent as follows:

"The invention comprises a method of neutralizing the organic acidity in heavy gas oils to produce a neutralization number less than 1.0 whereby they are rendered suitable as lube oil feed stocks which comprises treating said heavy gas oils with a neutralizing amount of monoethanolamine to form an amine salt with the organic acids and then heating the thus-neutralized heavy gas oil at a temperature and for a time sufficient to convert the amine salts to amides."

"The amount of monoethanolamine necessary to produce neutralization of a heavy gas oil which has a neutralization number greater than 1.0 can best be determined by using titration techniques or by trial and error."

"As indicated, after the amine has been added to the oil and salt formation occurs, the salts should be converted substantially to their amides. This can be done at temperatures about 25° F. greater than the boiling point of water for a period of time ranging over several days or higher temperatures can be employed and shorter reaction times used. Typically, if one were to heat the salt product at about 400°-500° F. for between 1-2 hours, the amide formation would take place."

The organic acidity present in the heavy gas oils are primarily naphthenic acids.

The present invention relates to the amides produced by the above described process as compositions of matter.

THE NAPHTHENIC ACIDS

Naphthenic acids are described in Kirk-Othmer's *Encyclopedia of Chemical Technology*, Third Edition, Volume 15, John Wiley & Sons, 1981, the disclosure of which is incorporated herein by reference.

The naphthenic acids obtained from petroleum and its distillates have hydrocarbon components corresponding generally to the hydrocarbon components of petroleum or its distillates from which they were derived. Preferred sources are the naphthenic acids found in gas oils, particularly heavy gas oils.

THE AMINES

The starting amines have the structural formula:

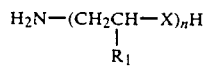

Formula I where
$R_1$ is H or Me,
X is chosen, at each occurrence, from O or NH, and
n is a small whole number of from 1-10.

In the above formula, when X is O, n is preferably 1. When X is NH, n is preferably 2 or more.

In addition to the structures defining the starting amines above, it is also understood that the formulas above also represent linear, branched and cyclic congenors of the structures mentioned above. For example, these starting amines may contain such compounds as aminoethyl piperazine, triethylene tetramine, diethylene triamine, and other structures which are branched or cyclic congenors of the above formulas. A preferred material is a commercially available compound or mixture of compounds which contain about 60 weight percent amino ethyl piperazine, about 25 weight percent triethylene tetramine, about 2 weight percent diethylene triamine, and about 12 weight percent of other admixtures of linear, branched and cyclic congenors of the above defined structures.

THE AMIDES

The amides of the invention have the formula:

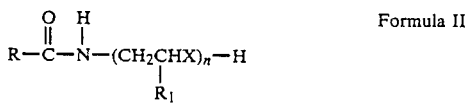

Formula II where R is the hydrocarbon portion of a naphthenic acid of the type previously described, and $R_1$, X, and n have the values previously described in Formula I.

Again, as above, the amides of the invention having the formula defined as Formula II, also are understood to contain multiple amide substitution where the amino compounds of the starting amines permit such a substitution. For example, diamides may be formed by reacting naphthenic acids with starting amines which have multiple free amino functional groups. These diamides would also be expected to have usefulness in performing the corrosion inhibition found to be important for these amides. These diamides are formed particularly when X is at least 1 NH group, whether or not X can also be more than 1 or X may also be represented by oxygen in higher molecular weight compounds.

In performing the steps described in U.S. Pat. No. 4,589,979, the amides of the invention are produced. During the formation of the amides a back pressure may be required. The amount of back pressure is related to the vapor pressure of the amine and may be determined by trial and error; however, at temperatures above 600° F., the back pressure required for formation of adequate effective amounts of our amide are predictably higher.

After the reaction is completed and the amides formed, they may potentially be separated from the petroleum or petroleum fraction by using conventional separation techniques such as solvent extraction which may employ either organic solvents or water. The most preferable method of extracting and isolating the amides comprises distillation, preferably vacuum distillation to separate the amides from the petroleum or the petroleum fraction.

A typical method for preparing the amides from a gas oil is set forth below:

A virgin gas oil was selected from a refinery located in the southern part of the United States. The neutralization number of this gas oil was 3.54. The neutralization number was determined using the well-known ASTM procedure D-974.

To determine the effectiveness of different amines at lowering the neutralization number, a weighed amount of the test vacuum gas oil and the additive were fluxed at between 450°–500° F. for 1.5 hours. This converted the salt formed by neutralization to the amide.

Using the above test procedure, the results are presented below in the Table.

TABLE 1

| Additive | Concentration | Neutralization Number |
|---|---|---|
| Blank | — | 3.54 |
| Polyamine* Bottoms | 1.43% | 2.45 |
| Polyamine Bottoms | 2.86% | 1.90 |
| Polyamine Bottoms | 6.0% | 1.20 |
| Tetraethylene** Pentamine | 2.0% | 0.54 |
| Tetraethylene Pentamine | 1.0% | 0.82 |
| Monoethanolamine | 0.3% | 1.63 |
| Monoethanolamine | 0.45% | 1.22 |
| Monoethanolamine | 0.6% | 0.82 |

*A mixture of aliphatic and heterocyclic amines with boiling range between 410–465° F., Sp. G. ranging between 0.98–1.09 with multiple amine substituents.
**A mixture containing: 65 weight percent of major isomers
1. linear triethylene pentamine
2. linear tetra ethylene pentamine
3. amino ethyl tris-amino ethylamine
4. amino ethyl diamino ethyl piperazine
5. aminoethyl piperazino ethyl ethylene diamine
6. piperazino ethyl diamino ethyl amine
7. bis-piperazino ethyl diamino ethyl amine, and 25 weight percent of the following major isomers:
(1) linear triethylene tetramine
(2) tris-amino ethylamine
(3) piperazino ethyl ethylene diamine
(4) bis-aminoethyl piperazine, and about 10 weight percent of:
1. pentaethylene hexamine
2. other linear, branched, and cyclic congenors of similar amino structures.

The gas oil containing the amide would then be vacuum distilled and the amide residue would be recovered.

Having thus described our invention, we claim:

1. A method of producing naphthenic acid amides having the formula:

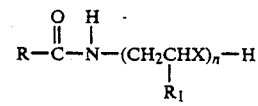

wherein
R is the hydrocarbon portion of a naphthenic acid from a petroleum or a petroleum fraction.
$R_1$ is H or Methyl,
X is chosen, at each occurrence, from O or NH, and
n is an integer ranging from 1–10; which method comprises reacting an amine of the formula:

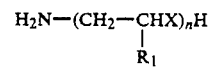

wherein $R_1$, X and n have the meanings above, with
(a) a petroleum fraction containing naphthenic acids thereby forming a naphthenic acid-amine salt of said amine and said naphthenic acid in the petroleum fraction; and then
(b) heating the petroleum fraction containing the naphthenic acid-amine salt to a temperature of at least 35° F. greater than the boiling point of water for a time sufficient to convert the naphthenic acid-amine salt to the naphthenic acid amides and then,
(c) recovering the thus produced amides.

* * * * *